US012708652B2

(12) United States Patent
Murakami et al.

(10) Patent No.: US 12,708,652 B2
(45) Date of Patent: Aug. 18, 2026

(54) SLEEP PROMOTING COMPOSITION, AND FOOD PRODUCT, MEDICINAL PRODUCT, AND ANIMAL FEED CONTAINING SAID COMPOSITION

(71) Applicant: MEGMILK SNOW BRAND Co., Ltd., Hokkaido (JP)

(72) Inventors: Hiroki Murakami, Hokkaido (JP); Taro Ko, Hokkaido (JP); Hiroshi Ishimoto, Aichi (JP); Azusa Kamikouchi, Aichi (JP); Ikue Mori, Aichi (JP)

(73) Assignee: MEGMILK SNOW BRAND Co., Ltd., Hokkaido (JP)

( * ) Notice: Subject to any disclaimer, the term of this patent is extended or adjusted under 35 U.S.C. 154(b) by 675 days.

(21) Appl. No.: 17/797,691

(22) PCT Filed: Jan. 26, 2021

(86) PCT No.: PCT/JP2021/002647
§ 371 (c)(1),
(2) Date: Aug. 4, 2022

(87) PCT Pub. No.: WO2021/157434
PCT Pub. Date: Aug. 12, 2021

(65) Prior Publication Data

US 2023/0085298 A1 Mar. 16, 2023

(30) Foreign Application Priority Data

Feb. 5, 2020 (JP) ................................. 2020-018148

(51) Int. Cl.
*A61K 35/747* (2015.01)
*A23K 10/18* (2016.01)
(Continued)

(52) U.S. Cl.
CPC ............ *A61K 35/745* (2013.01); *A23K 10/18* (2016.05); *A23L 33/135* (2016.08);
(Continued)

(58) Field of Classification Search
None
See application file for complete search history.

(56) References Cited

FOREIGN PATENT DOCUMENTS

CN 108671135 A 10/2018
CN 108823125 A 11/2018
(Continued)

OTHER PUBLICATIONS

Wu, Qian Qian, et al. "Changes in growth and survival of Bifidobacterium by coculture with Propionibacterium in soy milk, cow's milk, and modified MRS medium." International journal of food microbiology 157.1 (2012): 65-72. (Year: 2012).*
(Continued)

*Primary Examiner* — Thane Underdahl
*Assistant Examiner* — Mary A Crum
(74) *Attorney, Agent, or Firm* — Dinsmore & Shohl LLP

(57) ABSTRACT

An object of the present invention is to provide a composition for promoting sleep, that enables an increase of the sleep amounts in the overall night and in the initial stage of the night, a decrease of the sleep onset latent time, and an increase of the length of a sleep episode, and that is excellent in the stability and the safety. Another object of the present invention is to provide a food, a drug, and a feed that each include the composition for promoting sleep. The composition for promoting sleep is characterized in that the composition for promoting sleep includes a microorganism belonging to either *Bifidobacterium adolescentis* or *Lactobacillus plantarum*, or a culture thereof as an active ingredient.

7 Claims, 7 Drawing Sheets

(Wilcoxon-Mann-Whitney Test. It is determined for p<0.05 that a significant difference is present.)

(51) Int. Cl.

| | |
|---|---|
| ***A23L 33/135*** | (2016.01) |
| ***A61K 35/745*** | (2015.01) |
| ***A61P 25/20*** | (2006.01) |

(52) U.S. Cl.

CPC ............ *A61K 35/747* (2013.01); *A61P 25/20* (2018.01); *A23V 2002/00* (2013.01); *A23V 2400/169* (2023.08); *A23V 2400/513* (2023.08)

(56) References Cited

FOREIGN PATENT DOCUMENTS

| | | | | |
|---|---|---|---|---|
| CN | 109200065 | A | | 1/2019 |
| CN | 109965170 | A | | 7/2019 |
| CN | 110106122 | A | | 8/2019 |
| CN | 110537704 | A | * | 12/2019 |
| JP | 4527922 | B2 | | 6/2003 |
| JP | 2013121961 | A | | 6/2013 |
| JP | 5943342 | B2 | | 9/2013 |
| JP | 6279714 | B2 | | 4/2017 |
| WO | 0174352 | A1 | | 10/2001 |
| WO | 2019/123328 | A1 | | 6/2019 |
| WO | 2019/123329 | A1 | | 6/2019 |

OTHER PUBLICATIONS

Extended European Search Report for European Patent Application No. 21750538.7, dated Jan. 18, 2024.

Decision of Rejection for Chinese Patent Application No. 202180013392.3, dated Sep. 15, 2024.

Notification of Transmittal of Translation of the International Preliminary Report on Patentability (Chapter I or Chapter II of the Patent Cooperation Treaty), PCT Application No. PCT/JP2021/002647, Aug. 18, 2022.

Translation of the International Preliminary Report on Patentability, PCT Application No. PCT/JP2021/002647, Aug. 18, 2022.

Translation of the Written Opinion of the International Searching Authority, PCT Application No. PCT/JP2021/002647, Aug. 18, 2022.

English translation of the Opinion Portion of the Notice of First Examination Opinion for Chinese Application No. 2021800133923, dated Oct. 11, 2023.

Notice of First Examination Opinion for Chinese Application No. 2021800133923, dated Oct. 11, 2023.

Chinese Office Action for Chinese Patent Application No. 202180013392.3, dated Apr. 3, 2024.

English translation of Second Office Action for Chinese Patent Application No. 202180013392.3, dated Apr. 3, 2024.

International Search Report and Written Opinion for Application No. PCT/JP2021/002647, mailed Apr. 13, 2021, 10 pages.

Decision of Refusal for Japanese Application No. 2020-018148, dated Nov. 26, 2020, 12 pages.

Notice of Reasons for Refusal for Japanese Application No. 2020-018148, dated Mar. 31, 2020, 8 pages.

Notice of Reasons for Refusal for Japanese Application No. 2020-018148, dated Aug. 3, 2020, 8 pages.

* cited by examiner (Wilcoxon-Mann-Whitney Test. It is determined for p<0.05 that a significant difference is present.)

(Wilcoxon-Mann-Whitney Test. It is determined for p<0.05 that a significant difference is present.)

(Wilcoxon-Mann-Whitney Test. It is determined for p<0.05 that a significant difference is present.)

(Wilcoxon-Mann-Whitney Test. It is determined for $p<0.05$ that a significant difference is present.)

(Wilcoxon-Mann-Whitney Test. It is determined for $p<0.05$ that a significant difference is present.)

(Wilcoxon-Mann-Whitney Test. It is determined for p<0.05 that a significant difference is present.)

(Wilcoxon-Mann-Whitney Test. It is determined for p<0.05 that a significant difference is present.)

(Wilcoxon-Mann-Whitney Test. It is determined for $p<0.05$ that a significant difference is present.)

(Wilcoxon-Mann-Whitney Test. It is determined for $p<0.05$ that a significant difference is present.)

(Wilcoxon-Mann-Whitney Test. It is determined for p<0.05 that a significant difference is present.)

(Wilcoxon-Mann-Whitney Test. It is determined for p<0.05 that a significant difference is present.)

(Wilcoxon-Mann-Whitney Test. It is determined for p<0.05 that a significant difference is present.)

SLEEP PROMOTING COMPOSITION, AND FOOD PRODUCT, MEDICINAL PRODUCT, AND ANIMAL FEED CONTAINING SAID COMPOSITION

TECHNICAL FIELD

The present invention relates to a composition for promoting sleep, that is capable of promoting sleep and that is excellent in the stability and the safety. The present invention also relates to a food, a drug, and a feed that each include the composition for promoting sleep.

BACKGROUND ART

Sleep is a behavior that is necessary for an animal to live, and a sleep state or a sleep-like state is present for not only mammals but also non-mammalian species such as fish, flies, and nematode worms. Due to the change of the lifestyle, the life rhythm has recently been disordered and the prevalence of a sleep disorder such as insomnia has increased. According to a survey by the Ministry of Health, Labor and Welfare, one out of five has some trouble related to sleep (Non-Patent Document 1). It has turned out that a sleep disorder is closely related not only to a decrease of the labor productivity due to e.g., drowsiness but also to mental disorders such as dementia and depression, and lifestyle-related diseases such as obesity and diabetes. The economic loss caused by the insufficient sleep is estimated to be about 3.5 trillion Japanese yen (Non-Patent Document 2).

Use of a sleeping drug that is a medicine can be considered for a person with a sleep disorder such as insomnia. A barbituric acid-based sleeping drug, a benzodiazepine-based sleeping drug, and a non-benzodiazepine sleeping drug are mainly used as the sleeping drugs. It is known that the barbituric acid-based sleeping drug however has strong side effects such as dependence, and the sleep caused by the benzodiazepine-based sleeping drug shows non-physiological EEG-patterns with benzodiazepine fast wave, and the benzodiazepine-based sleeping drug does not therefore induce any physiological and high-quality sleep.

From the above, a material capable of being taken in daily instead of a medicine and capable of inducing a physiological sleep has been actively developed, and various types of the material have been proposed from natural ingredients, food ingredients, and the like. For example, an agent for improving disorders of sound-sleep based on glycine that is an amino acid (Patent Document 1) and a sleep promoting composition based on theanine (Patent Document 2) are present. Among lactic acid bacteria that have been used in fermented foods from long ago and that are highly safe to the biological body, a sleep promoting activity (improvement of the quality of sleep by increasing the REM sleep and decreasing the non-REM sleep) by specific strains of *Lactobacillus acidophilus, Lactobacillus helveticus*, and *Streptococcus thermophilus* that are non-pathogenic lactic acid bacteria (Patent Document 3), a sleep quality improving agent based on *Lactobacillus casei* (Patent Document 4), and a circadian rhythm improving agent based on *Lactobacillus brevis* (Patent Document 5) are known.

It however still cannot be stated that sufficient options are present to satisfy the various needs of the consumers.

*Drosophila melanogaster* (hereinafter, referred to as "fruit fly") is used as a model organism in various fields of biology. The overall genome thereof was determined in 2000 and it is estimated that about 75% of the genes related to human disease are also present in fruit fly. Fruit fly that is a disease model has recently been developed for each of Alzheimer's disease, Parkinson's disease, the metabolic syndrome, and the like and is actually used in finding out the disease onset mechanism and screening of therapeutic drugs (Patent Documents 3 and 4).

Many studies each using fruit fly have been conducted in the field of sleep study, and it has turned out not only that fruit fly shows a sleep-like behavior similar to that of the human but also that the feature thereof and many of its molecular bases are common to those of the sleep of mammals (Non-Patent Documents 5 and 6). It has been reported as specific examples that variation of the sleep mode depending on the age (Non-Patent Document 7), the homeostasis mechanism of sleep (a sleep behavior to compensate lost sleep) (Non-Patent Document 8), an awakening action of caffeine (Non-Patent Document 9), a sleep promoting action of glycine (Non-Patent Document 10), and a sleep-wake control action of neurotransmitters such as dopamine, serotonin, GABA, and the like, and EGF (Non-Patent Documents 11, 12 and 13) are common between fruit fly and mammals. It is known furthermore that the neural circuit related to sleep has been preserved in the course of the evolution in spite of the difference in the nerve system structure such as the facts that the para intercerebralis of fruit fly that is embryologically and functionally similar to the hypothalamic area of mammals plays an important role for sleep and that the wake-promoting neural circuit and the sleep-promoting neural circuit mutually communicate with each other in fruit fly similar to those of mammals (Non-Patent Documents 5 and 6).

It is considered from the above that fruit fly is suitable as a model organism for studies on sleep and is also useful for the quest for the substance involved in the sleep control (Non-Patent Documents 5 and 6).

CITATION LIST

Patent Literature

[Patent Document 1] JP 2013-121961 A
[Patent Document 2] WO 01/074352 A
[Patent Document 3] JP 4,527,922 B
[Patent Document 4] JP 6,279,714 B
[Patent Document 5] JP 5,943,342 B

Non Patent Literature

[Non-Patent Document 1] National Health and Nutrition Survey 2009, Ministry of Health, Labour and Welfare
[Non-Patent Document 2] Makoto Uchiyama, Journal of Japan Psychiatric Hospital Association 31(11), 1163-1169, 2012-11, 2012
[Non-Patent Document 3] Pandey, U. B. & Nichols, C. D. Human Disease Models in *Drosophila melanogaster* and the Role of the Fly in Therapeutic Drug Discovery. Drug Deliv. 63, 411-436 (2011)
[Non-Patent Document 4] Ugur, B., Chen, K. & Bellen, H. J. *Drosophila* tools and assays for the study of human diseases. Dis. Model. Mech. 9, 235-244 (2016).
[Non-Patent Document 5] Zimmerman, J. E., Naidoo, N., Raizen, D. M. & Pack, A. I. Conservation of sleep: insights from non-mammalian model systems. Trends Neurosci. 31, 371-376 (2008).
[Non-Patent Document 6] Ly, S., Pack, A. I. & Naidoo, N. The neurobiological basis of sleep: Insights from *Drosophila*. Neurosci. Biobehav. Rev. 87, 67-86 (2018).

[Non-Patent Document 7] Koh, K., Evans, J. M., Hendricks, J. C. & Sehgal, A. A *Drosophila* model for age-associated changes in sleep:wake cycles. Proc. Natl. Acad. Sci. U.S.A. 103(37), 13843-13847 (2006)

[Non-Patent Document 8] Huber, R. et al. Sleep homeostasis in *Drosophila melanogaster*. Sleep 27, 628-639 (2004)

[Non-Patent Document 9] Wu, M. N. et al. The effects of caffeine on sleep in *Drosophila* require PKA activity, but not the adenosine receptor. J Neurosci 29(35), 11029-11037 (2009)

[Non-Patent Document 10] Kazuhiko Kume, Exploring novel sleep regulation mechanisms using *Drosophila melanogaster*, Proceedings of the Uehara Memorial Foundation for Life Sciences. 30(2016)

[Non-Patent Document 11] Ueno, T. et al. Identification of a dopamine pathway that regulates sleep and arousal in *Drosophila*. Nat. Neurosci. 15, 1516-1523 (2012)

[Non-Patent Document 12] Sehgal, A. & Mignot, E. Genetics of sleep and sleep disorders. Cell. 146, 194-207 (2011).

[Non-Patent Document 13] Foltenyi, K et al. Neurohormonal and neuromodulatory control of sleep in *Drosophila*. Cold Spring Harb Symp Quant Biol. 72, 565-571 (2007)

SUMMARY OF INVENTION

Technical Problem

An object of the present invention is to provide a composition for promoting sleep, that is capable of promoting sleep and that is excellent in the stability and the safety. Another object of the present invention is to provide a food, a drug, and a feed that each include the composition for promoting sleep.

Solution to Problem

The inventors vigorously conducted studies to solve the problems, and have found that a plurality of microorganisms promote sleep.

The present invention includes the following aspects.

(1) A sleep-promoting composition including one or more microorganism(s) that belong(s) to any one of the species *Bifidobacterium adolescentis* and the species *Lactobacillus plantarum*.

(2) The sleep-promoting composition according to (1), wherein the sleep-promoting composition is one or more selected from a sleep amount-increasing composition, a sleep induction-promoting composition, and a sleep quality-improving composition.

(3) The sleep-promoting composition according to (2), wherein the sleep-promoting composition is the sleep amount-increasing composition.

(4) The sleep-promoting composition according to (2), wherein the sleep-promoting composition is the sleep induction-promoting composition.

(5) The sleep-promoting composition according to (2), wherein the sleep-promoting composition is the sleep quality-improving composition.

(6) The sleep-promoting composition according to any one of (1) to (5), wherein the species *Bifidobacterium adolescentis* is a strain *Bifidobacterium adolescentis* SBT0430 or a strain *Bifidobacterium adolescentis* SBT2786.

(7) The sleep-promoting composition according to any one of (1) to (5), wherein the species *Lactobacillus plantarum* is a strain *Lactobacillus plantarum* SBT2227.

(8) A sleep-promoting food, a sleep-promoting drug, or a sleep-promoting feed that includes the sleep-promoting composition according to any one of (1) to (7).

(9) A strain *Bifidobacterium adolescentis* SBT0430 whose accession number is NITE BP-03103, a strain *Bifidobacterium adolescentis* SBT2786 whose accession number is NITE BP-03102, a strain *Lactobacillus plantarum* SBT2227 whose accession number is NITE BP-03104.

Advantageous Effects of Invention

The present invention provides the composition for promoting sleep capable of promoting sleep, and the expression "promote sleep (sleep promoting)" as used herein refers to the fact that an increase of the sleep amount (an increase of the sleep amount in a night), promotion of sleep induction (an increase of the sleep amount in the initial stage of a night, and a decrease of the sleep onset latent time), and improvement of the sleep quality (an increase of deep sleep like that represented by an increase of the length of the longest sleep episode) can be realized. In an aspect, the present invention therefore provides a sleep amount-increasing composition, a sleep induction promoting composition, and/or a sleep quality-improving composition.

DESCRIPTION OF EMBODIMENTS

Figure 1:
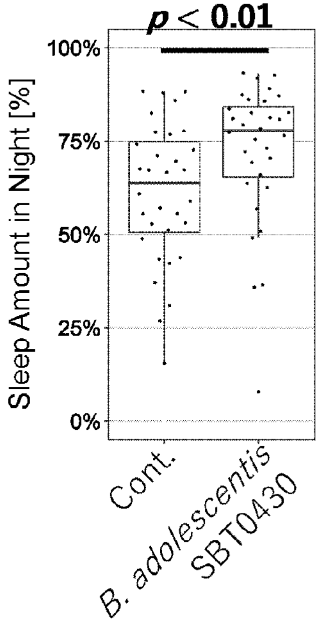
FIG. 1 is a diagram depicting the sleep amount in an overall night of fruit fly fed the *Bifidobacterium adolescentis* SBT0430 strain.

A composition for promoting sleep of the present invention will be described. Any substance can be used as an active ingredient of the present invention as long as the substance is a microorganism belonging to the species *Bifidobacterium adolescentis* or the species *Lactobacillus plantarum* and achieves effects of improving the maintenance of sleep and promoting the sleep induction.

The strain of the microorganism is not especially limited as long as the microorganism is the species *Bifidobacterium adolescentis* or the species *Lactobacillus plantarum* while the preferred examples thereof include the SBT0430 strain and the SBT2786 strain for the species *Bifidobacterium adolescentis*, and the SBT2227 strain for the species *Lactobacillus plantarum.*

These three strains are all internationally deposited in International Patent Organisms Depositary (IPOD), and Table 1 shows their receipt numbers.

TABLE 1

| Strain Receipt Number | | |
|---|---|---|
| Name of Bacterial Species | Name of Strain | Receipt Number |
| *Bifidobacterium adolescentis* | SBT0430 | NITE ABP-03103 |
| *Bifidobacterium adolescentis* | SBT2786 | NITE ABP-03102 |
| *Lactobacillus plantarum* | SBT2227 | NITE ABP-03104 |

These microorganisms may each be used alone, or two or more species thereof may be used in combination as necessary.

Microorganisms can be cultured by employing conditions suitable for each microorganism. Various types of culture medium are each usable as the culture medium such as, for example, a milk medium or a culture medium including a milk component, a semi-synthetic medium including no milk component, and a chemically specified synthetic medium. Examples of these culture media can include a reconstituted skim milk and an MRS medium.

The bacterial cells separated from the acquired culture using a harvesting means such as centrifugal separation can be used as it is as the active ingredient of the present invention. It is preferred that living bacterial cells be used while some treatment may be applied to the bacterial cells. The bacterial cells that are frozen, dried, freeze-dried, or the like can be used or the bacterial cells may be heat-dried to acquire dead bacterial cells, and the processing method is not especially limited. Not only those purely separated as the bacterial cells but also a culture, a suspension, another bacterial cell-including stuff, and a cytoplasm or a cell wall fraction that is acquired by treating the bacterial cells using an enzyme or a physical means are also usable.

Examples of the form of the culture and the like include not only a culture acquired by using a culture medium generally used in culturing a lactic acid bacterium such as an MRS culture medium (manufactured by DIFCO) that is a synthetic medium or a reconstituted skim milk culture medium but also a dairy product such as a cheese, a fermented milk, or a dairy product lactic acid bacterium beverage while the form is not especially limited.

The composition for promoting sleep of the present invention can be added to a food, a drug, a feed, and the like. In this case, the composition for promoting sleep of the present invention may be used as it is while, because the composition for promoting sleep is usable together with other raw materials usually included in the food, the drug, and the feed, the composition for promoting sleep can also be used in a powdered formulation, a granule formulation, a tablet formulation, an encapsulated formulation, a drinkable formulation, and the like, according to ordinary methods. The composition for promoting sleep can also be blended into foods and beverages such as a yogurt, a milk beverage, and a wafer, and a feed.

In the case where the composition for promoting sleep of the present invention is blended into a food, a drug, or a feed, the blending ratio of the microorganism is not especially limited and only has to be regulated as necessary to match with the easiness of the manufacture and a preferable dose per day. The blending amount is individually determined for each subject to be administered taking into consideration the symptom, the age, and the like of the person while, in the case of an ordinary adult human, the blending amount and the like only have to be adjusted to be able to take in the culture of the microorganism by 10 to 200 g, 20 to 200 g, 50 to 200 g, 100 to 200 g, 150 to 200 g, 20 to 150 g, 50 to 150 g, 100 to 150 g, or 50 to 100 g, or the bacterial cell itself of the microorganism by 0.1 to 5000 mg, 0.2 to 5000 mg, 0.5 to 5000 mg, 1 to 5000 mg, 2 to 5000 mg, 5 to 5000 mg, 10 to 5000 mg, 20 to 5000 mg, 50 to 5000 mg, 100 to 5000 mg, 200 to 5000 mg, 500 to 5000 mg, 1000 to 5000 mg, 2000 to 5000 mg, 0.2 to 2000 mg, 0.5 to 2000 mg, 1 to 2000 mg, 2 to 2000 mg, 5 to 2000 mg, 10 to 2000 mg, 20 to 2000 mg, 50 to 2000 mg, 100 to 2000 mg, 200 to 2000 mg, 500 to 2000 mg, 1000 to 2000 mg, 0.5 to 1000 mg, 1 to 1000 mg, 2 to 1000 mg, 5 to 1000 mg, 10 to 1000 mg, 20 to 1000 mg, 50 to 1000 mg, 100 to 1000 mg, 200 to 1000 mg, 500 to 1000 mg, 1 to 500 mg, 2 to 500 mg, 5 to 500 mg, 10 to 500 mg, 20 to 500 mg, 50 to 500 mg, 100 to 500 mg, 200 to 500 mg, 2 to 200 mg, 5 to 200 mg, 10 to 200 mg, 20 to 200 mg, 50 to 200 mg, 100 to 200 mg, 5 to 100 mg, 10 to 100 mg, 20 to 100 mg, 50 to 100 mg, 10 to 50 mg, or 20 to 50 mg. A desired effect can be achieved by taking in as above.

(Evaluation Method for Sleep Promoting Action of Composition for Promoting Sleep)

The sleep promoting action of the composition for promoting sleep of the present invention can be confirmed by an animal experiment using fruit fly as the subject described in Examples.

The present invention will be described below in detail with reference to Examples and Test Examples while these are only simply exemplifications and the present invention is not limited at all by these.

EXAMPLES (Test Example 1) Sleep Promoting Action of Microorganism

A sleep promoting action was evaluated using fruit fly for each of the *Bifidobacterium adolescentis* SBT0430 and SBT2786 strains, and the *Lactobacillus plantarum* SBT2227 strain.

1. Test Method (1) Provided Bacteria

The *Bifidobacterium adolescentis* SBT0430 and SBT2786 strains, and the *Lactobacillus plantarum* SBT2227 strain were used as the provided bacteria.

(2) Preparation of Provided Bacterium Bacterial Cells

Each of the provided bacteria in above (1) was cultured under the conditions shown in Table 2 (OD600=0.7 or higher), and the bacterial cell were thereafter separated using centrifugal separation (7000)×g, 4° C., 20 min). The bacterial cell were washed twice using a normal saline solution and was thereafter suspended in a 12.5%-trehalose solution in one tenth amount of the culture amount. This suspended solution was further mixed with an equal amount thereto of a 2%-agar and 10%-sucrose solution to produce a feed that included the provided bacterium bacterial cells.

(3) Test Procedure

A wild-type fruit fly $CS^{2202u}$ line was bred at a temperature of 25° C. and at a light and dark cycle of 12 hours. Unmated female individuals acquired five days after their adult eclosion were used in the evaluation. The fruit flies were placed in a glass tube having the diameter of 5 mm together with the feed in the above (2) (a test group) or together with a feed that included agar at 1%, sucrose at 5%, and no lactic acid bacterium (a control group), and their behaviors were measured for three days using a *Drosophila* activity monitoring system (manufactured by Trikinetics) for measuring the behaviors of the fruit fly. It is defined for fruit fly that the case where an immobility period (that is a period for the fruit fly to be static) continues for five minutes or longer is "sleep". The median value was therefore calculated for each of the sleep amount in the overall night (the period during which the lighting was turned off), the sleep amount in the first three hours of a night, the time period from the start of a night to observation of the first sleep episode, and the length of the longest sleep episode in a night to compare the test group and the control group with each other. The sleep amount is the amount of the total sleep time observed in the observation period (the daytime or the nighttime). An increase of the sleep amount in the overall night indicates promotion of sleep by increasing the sleep amount in the night. An increase of the sleep amount in the first three hours of a night indicates promotion of sleep induction. The time period from the start of a night to observation of the first sleep episode (latency to the first sleep bout) is called "sleep onset latent time" and a decrease of this time period also indicates promotion of sleep induction. An increase of the length of the longest sleep episode (the longest sleep bout) in a night indicates that the sleep is deep, that is, the sleep quality is improved. The evaluation was conducted using about 96 fruit flies in each of the groups, and presence or absence of any significant difference was evaluated using the Wilcoxon rank-sum test. It was determined that a significant difference was present with $p<0.05$ and a tendency for significance was present with $p<0.1$.

TABLE 2

Provided Bacteria and Culture Conditions

| Bacterial Species | Strain Number | Culture Medium | Culture Time Period | Culture Temperature |
|---|---|---|---|---|
| *Bifidobacterium adolescentis* | SBT0430 | GAM + G *1 | 37° C. (Anaerobic *3) | 20 h |
| *Bifidobacterium adolescentis* | SBT2786 | GAM + G *1 | 37° C. (Anaerobic *3) | 18 h |
| *Lactobacillus plantarum* | SBT2227 | MRS *2 | 37° C. (Anaerobic *3) | 16 h |

*1 CAM + G: A GAM culture medium (Manufactured by Nissui Pharmaceutical Co., Ltd.) + glucose at 1% (manufactured by FUJIFILM Wako Pure Chemical Corporation).
*2 MRS: An MRS culture medium.

*3 Anaerobic: The culture was conducted under an anaerobic condition using AneroPack (manufactured by Mitsubishi Gas Chemical Company, Inc.)

2. Test Result

Figure 2:
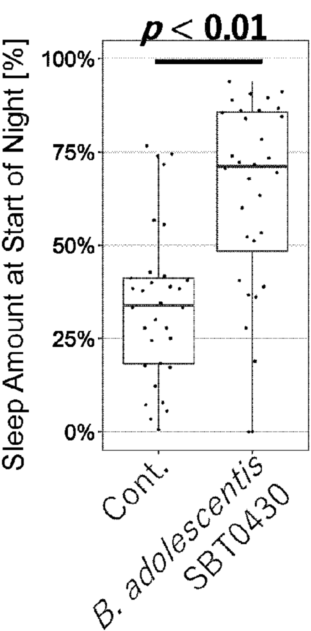
FIG. 2 is a diagram depicting the sleep amount in the first three hours of a night of fruit fly fed the *Bifidobacterium adolescentis* SBT0430 strain.
Figure 3:
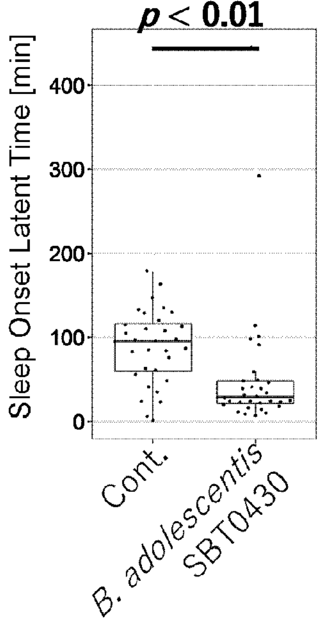
FIG. 3 is a diagram depicting a sleep onset latent time of fruit fly fed the *Bifidobacterium adolescentis* SBT0430 strain.
Figure 4:
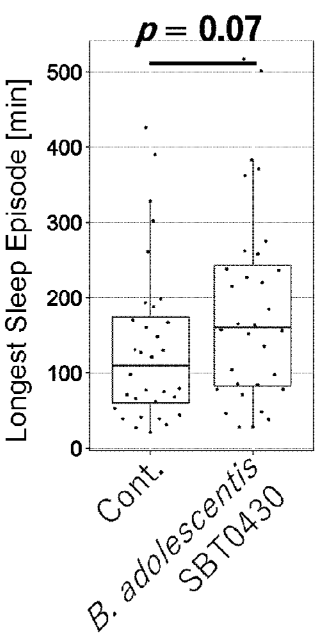
FIG. 4 is a diagram depicting the longest time of sleep episodes of fruit fly fed the *Bifidobacterium adolescentis* SBT0430 strain.

FIGS. 1 to 4 depict the result of the evaluation conducted for the *Bifidobacterium adolescentis* SBT0430 strain. As to the group that took in the *Bifidobacterium adolescentis* SBT0430 strain, a significant increase of the sleep amount in the night (FIG. 1), a significant increase of the sleep amount in the first three hours of the night (FIG. 2), a significant decrease of the sleep onset latent time (FIG. 3), and a significant increase tendency of the length of the longest sleep episode (FIG. 4) were recognized compared to the control group.

Figure 5:
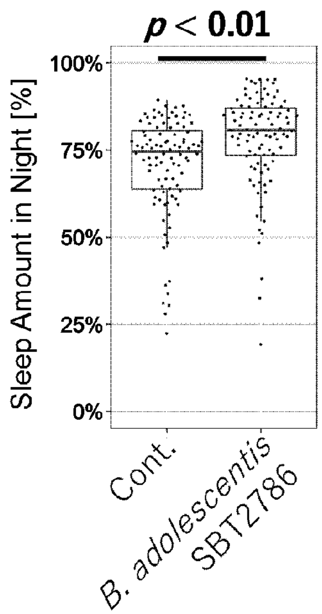
FIG. 5 is a diagram depicting the sleep amount in an overall night of fruit fly fed the *Bifidobacterium adolescentis* SBT2786 strain.
Figure 6:
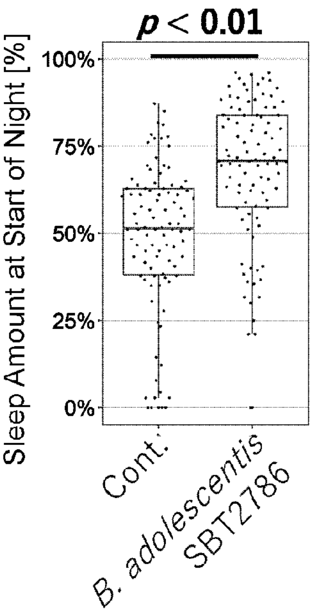
FIG. 6 is a diagram depicting the sleep amount in the first three hours of a night of fruit fly fed the *Bifidobacterium adolescentis* SBT2786 strain.
Figure 7:
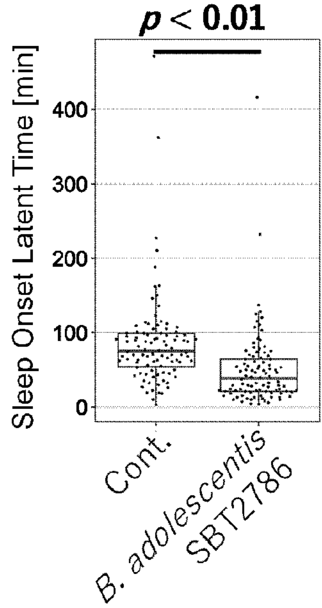
FIG. 7 is a diagram depicting the sleep onset latent time of fruit fly fed the *Bifidobacterium adolescentis* SBT2786 strain.
Figure 8:
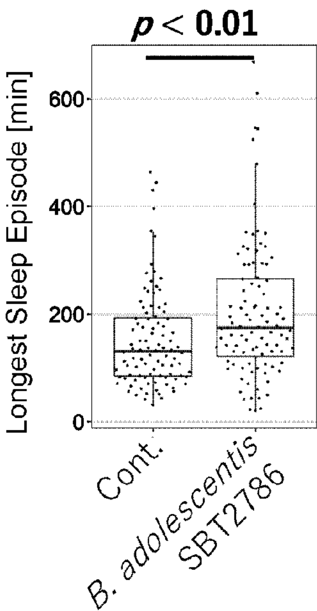
FIG. 8 is a diagram depicting the longest time of sleep episodes of fruit fly fed the *Bifidobacterium adolescentis* SBT2786 strain.

FIGS. 5 to 8 depict the result of the evaluation conducted for the *Bifidobacterium adolescentis* SBT2786 strain. As to the group that took in the *Bifidobacterium adolescentis SBT*2786 strain, a significant increase of the sleep amount in the night (FIG. 5), a significant increase of the sleep amount in the first three hours of the night (FIG. 6), a significant decrease of the sleep onset latent time (FIG. 7), and a significant increase of the length of the longest sleep episode (FIG. 8) were recognized compared to the control group.

Figure 9:
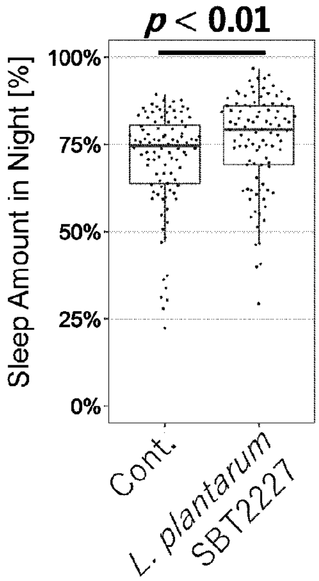
FIG. 9 is a diagram depicting the sleep amount in an overall night of fruit fly fed the *Lactobacillus plantarum* SBT2227 strain.
Figure 10:
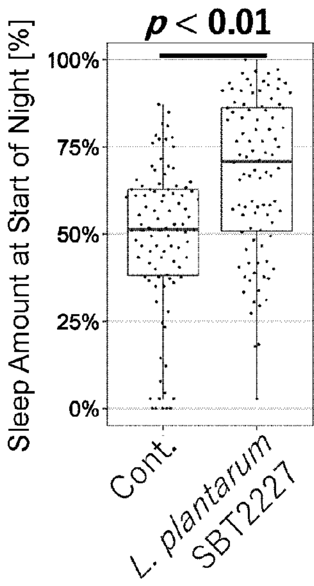
FIG. 10 is a diagram depicting the sleep amount in the first three hours of a night of fruit fly fed the *Lactobacillus plantarum* SBT2227 strain.
Figure 11:
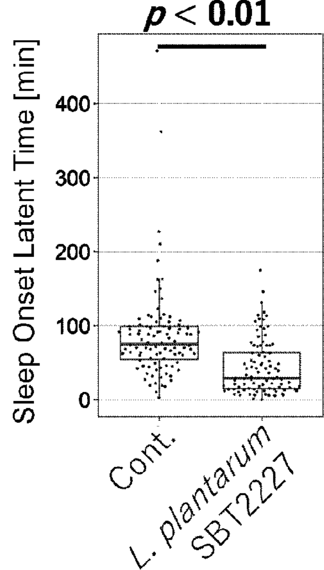
FIG. 11 is a diagram depicting a sleep onset latent time of fruit fly fed the *Lactobacillus plantarum* SBT2227 strain.
Figure 12:
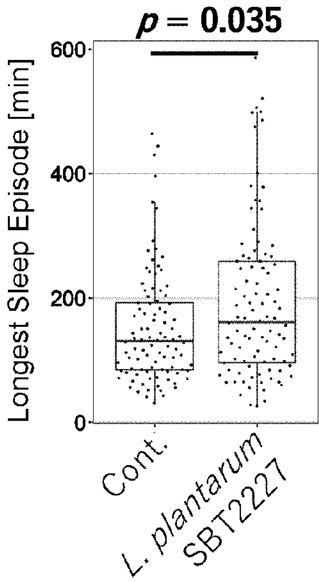
FIG. 12 is a diagram depicting the longest time of sleep episodes of fruit fly fed the *Lactobacillus plantarum* SBT2227 strain.

FIGS. 9 to 12 depict the result of the evaluation conducted for the *Lactobacillus plantarum* SBT2227 strain. As to the group that took in the *Lactobacillus plantarum* SBT2227 strain, a significant increase of the sleep amount in the night (FIG. 9), a significant increase of the sleep amount in the first three hours of the night (FIG. 10), a significant decrease of the sleep onset latent time (FIG. 11), and a significant increase of the length of the longest sleep episode (FIG. 12) were recognized compared to the control group.

From the above result, it was indicated that the *Bifidobacterium adolescentis* SBT0430 strain, the *Bifidobacterium adolescentis* SBT2786 strain, and the *Lactobacillus plantarum* SBT2227 strain each has an action of increasing the sleep amount, an action of promoting the sleep induction, and an action of improving the sleep quality.

(Example 1) Manufacture of Sleep Promoting Agent (Granules)

The *Lactobacillus plantarum* SBT2227 strain was inoculated at 5% by weight into an edible synthetic culture medium (to which a yeast extract at 0.5% and trypticase-peptone at 0.1% were added), the culture was conducted at 38° C. for 15 hours, and the bacterial cells were thereafter collected using centrifugal separation. The collected bacterial cells were freeze-dried to acquire freeze-dried powder of the bacterial cells. One gram (1 g) of the freeze-dried powder was mixed with 5 g of lactose and the mixture was shaped into granules to acquire the sleep promoting agent of the present invention.

(Example 2) Manufacture of Sleep Promoting Agent (Powdered Formulation)

In conformity to the provision in "Powdered Formulation" in the Drug Formulation General Provisions of the Practical Guide for Japanese Pharmacopoeia 13th Edition, 400 g of lactose (Japanese Pharmacopoeia) and 600 g pf potato starch (Japanese Pharmacopoeia) were added to 10 g of the freeze-dried powder of the *Lactobacillus plantarum* SBT2227 strain acquired in above Example 1, and these were uniformly mixed with each other to manufacture the sleep promoting agent of the present invention.

(Example 3) Manufacture of Nutritional Composition for Promoting Sleep

The *Lactobacillus plantarum* SBT2227 strain was inoculated at 5% by weight into an edible synthetic culture medium (to which a yeast extract at 0.5% and trypticase-peptone at 0.1% were added), the culture was conducted at 38° C. for 15 hours, and the bacterial cells were thereafter collected using centrifugal separation. The collected bacterial cells were freeze-dried. Forty grams (40 g) of freeze-dried powder of the freeze-dried powder was added to 40 g of vitamin C or 40 g of an equal-amount mixture of vitamin C and citric acid, 100 g of granulated sugar, and 60 g of an equal-amount mixture of corn starch and lactose to be mixed with each other. The mixture was packed in a bag to manufacture the nutritional composition for promoting sleep.

(Example 4) Manufacture of Beverage for Promoting Sleep

One gram (1 g) of the *Lactobacillus plantarum* SBT2227 strain acquired in Example 3 above was resolved in 699 g of deionized water and the solution was thereafter heated to 40° C. to thereafter be stirred and mixed at 9,500 rpm for 20 minutes using an ultra-disperser (ULTRA-TURRAX T-25 manufactured by IKA Japan). One-hundred grams (100 g) of maltitol, 2 g of an acidulant, 20 g of reduced starch syrup, 2 g of a flavoring agent, and 176 g of deionized water were added to the solution, and the acquired solution was thereafter put in 10 100-ml glass bottles to fill them up to be sterilized at 95° C. for 15 seconds. The glass bottles were airtight-plugged to manufacture 10 bottles (each containing 100 ml) of the beverage of the present invention.

(Example 5) Manufacture of Feed for Promoting Sleep

Twelve kilograms (12 kg) of soybean cake, 14 kg of powdered skim milk, 4 kg of soybean oil, 2 kg of corn oil, 23.2 kg of palm oil, 14 kg of corn starch, 9 kg of wheat flour, 2 kg of bran, 5 kg of a vitamin mixture, 2.8 kg of cellulose, and 2 kg of a mineral mixture were blended with each other to be sterilized at 120° C. for 4 minutes, and 10 kg of the *Lactobacillus plantarum* SBT2227 strain acquired in Example 3 was blended into the above mixture to manufacture the feed of the present invention.

(Example 6) Manufacture of Fermented Milk

The *Lactobacillus plantarum* SBT2227 strain was inoculated at 5% by weight into an edible synthetic culture medium (to which a yeast extract at 0.5% and trypticase-peptone at 0.1% were added), the culture was conducted at 37° C. for 17 hours, and the bacterial cells were thereafter collected using centrifugal separation to be freeze-dried. Five grams (5 g) of the freeze-dried bacterial cells, 1,700 g of powdered skim milk, 300 g of glucose, and 7,695 g of deionized water were mixed with each other and the mixture was heat-sterilized by being maintained at 95° C. for two hours. The mixture was cooled to 37° C. and 300 g of a lactic acid bacteria starter (Lb. *casei*) was inoculated into the mixture. The mixture was stirred and mixed, and was thereafter fermented until pH thereof reached to 4.0 in an incubator that was kept at 37° C. After pH thereof reached 4.0, the mixture was cooled to 10° C. or lower to manufacture 10 kg of the fermented milk of the present invention.

INDUSTRIAL APPLICABILITY

The present invention provides microorganisms belonging to the species *Bifidobacterium adolescentis* and the species *Lactobacillus plantarum*, a composition including each of the microorganisms, and a food, a drug, and a feed each including the composition, as a novel composition that promotes sleep. Taking in each of the composition and the like of the present invention enables promotion of sleep.

Accession Number

[Reference to Deposited Biological Material]

(1) *Bifidobacterium adolescentis* SBT2786 Strain (Receipt Number: NITEABP-03102, Date of Deposit: Jan. 13, 2021), Place of Deposit: National Institute of Technology and Evaluation of Products, Patent Microorganisms Depositary (NPMD), 2-5-8, Kazusakamatari, Kisarazu-shi, Chiba 292-0818 Japan (2) *Bifidobacterium adolescentis* SBT0430 Strain (Receipt Number: NITE ABP-03103, Date of Deposit: Jan. 13, 2021), Place of Deposit: National Institute of Technology and Evaluation of Products, Patent Microorganisms Depositary (NPMD), 2-5-8, Kazusakamatari, Kisarazu-shi, Chiba 292-0818 Japan (3) *Lactobacillus plantarum* SBT2227 Strain (Receipt Number: NITE ABP-03104, Date of Deposit: Jan. 13, 2021), Place of Deposit: National Institute of Technology and Evaluation of Products, Patent Microorganisms Depositary (NPMD), 2-5-8, Kazusakamatari, Kisarazu-shi, Chiba 292-0818 Japan

The invention claimed is:

1. A method for promoting sleep comprising administering to a subject in need thereof a composition comprising one or more microorganism(s) selected from *Bifidobacterium adolescentis* SBT0430 with accession number NITE BP-03103, *Bifidobacterium adolescentis* SBT2786 with accession number NITE BP-03102, or *Lactobacillus plantarum* SBT2227 with accession number NITE BP-03104, wherein the composition comprises:

cells of said microorganism(s) separated from a culture;

a culture of said microorganism(s) in a medium selected from:

a culture medium comprising milk component, a semi-synthetic medium including no milk component, a chemically defined synthetic medium, or de Man, Rogosa and Sharpe (MRS) culture medium;

a dairy product comprising said microorganism(s), wherein the diary product is selected from cheese, fermented milk, or a dairy beverage.

2. The method for promoting sleep according to claim 1, wherein promoting sleep is one or more selected from increasing sleep amount, promoting sleep induction, and improving sleep quality.

3. The method for promoting sleep according to claim 2, wherein promoting sleep comprises increasing sleep amount.

4. The method for promoting sleep according to claim 2, promoting sleep comprises promoting sleep induction.

5. The method for promoting sleep according to claim 2, promoting sleep comprises improving sleep quality.

6. The method of promoting sleep according to claim 1, wherein the microorganism is *Bifidobacterium adolescentis* SBT0430 with accession number NITE BP-03103 or *Bifidobacterium adolescentis* SBT2786 with accession number.

7. The method of promoting sleep according to claim 1, wherein the microorganism is *Lactobacillus plantarum* SBT2227 with accession number NITE BP-03104.

* * * * *